United States Patent
Lee et al.

(10) Patent No.: US 7,767,844 B2
(45) Date of Patent: Aug. 3, 2010

(54) METHOD FOR MANUFACTURING DIETHYLENE TRIAMINE PENTAACETIC ACID DERIVATIVE

(75) Inventors: Te-Wei Lee, Taoyuan (TW); Chia-Hsi Yang, Taoyuan (TW); Yen-Sheng Ho, Taoyuan (TW); Li-Hui Lu, Taoyuan (TW); Shu-Ling Chen, Taoyuan (TW)

(73) Assignee: Atomic Energy Council, Taoyuan (TW)

( * ) Notice: Subject to any disclaimer, the term of this patent is extended or adjusted under 35 U.S.C. 154(b) by 1168 days.

(21) Appl. No.: 11/134,397

(22) Filed: May 23, 2005

(65) Prior Publication Data

US 2006/0264669 A1    Nov. 23, 2006

(51) Int. Cl.
*C07C 229/00*    (2006.01)
*C07C 69/34*    (2006.01)

(52) U.S. Cl. .................. 560/169; 560/170; 560/190

(58) Field of Classification Search ............... 562/517, 562/553, 554, 590, 593
See application file for complete search history.

(56) References Cited

U.S. PATENT DOCUMENTS 5,376,357 A * 12/1994 Rajagopalan et al. ........ 540/474

FOREIGN PATENT DOCUMENTS

| JP | 11-308855 | 11/1999 |
| JP | 2000-125586 | 4/2000 |

* cited by examiner

*Primary Examiner*—Karl J Puttlitz
(74) *Attorney, Agent, or Firm*—Jackson IPG PLLC

(57) ABSTRACT

The present invention at first prepares a penta-alkyl DTPA and then processes a regioselective hydrolysis over the penta-alkyl DTPA while using a metal ion as a catalyst to obtain a tetra-alkyl DTPA, where, by the above two steps, a monoreactive DTPA derivative is manufactured.

13 Claims, 5 Drawing Sheets

$R = -C_2H_5$

R = –C₂H₅

R = –C$_2$H$_5$

R = (CH₃)₃C–

$R = (CH_3)_3C-$

METHOD FOR MANUFACTURING DIETHYLENE TRIAMINE PENTAACETIC ACID DERIVATIVE

FIELD OF THE INVENTION

The present invention relates to manufacturing a derivative; more particularly, relates to preparing a penta-alkyl DTPA (Diethylene Triamine Penta-acetic Acid) to be processed through a regioselective hydrolysis with a metal ion as a catalyst to obtain a tetra-alkyl DTPA, which is a monoreactive DTPA derivative, to be applied in related industries of imaging agents, medical services and chemistry.

DESCRIPTION OF THE RELATED ART

A DTPA is a bifunctional chelator, which can be conjugated with a protein and be labeled by a radioisotope to be applied in radiopharmaceutical, magnetic resonance imaging (MRI) and optical imaging. In a method for manufacturing a DTPA derivative according a prior art, a $^{111}$In-DTPA-folate, a 99 mTc-DTPA-folate, a $^{90}$Y-DTPA-D-Phe-Octreotide, or a $^{111}$In-DTPA-D-Phe-Octreotid is used as a receptor-target radio pharmaceutical; or, a Gd-DTPA is linked to neurotensin derivative to be a MRI agent.

Although the target molecule (such as peptide, protein, etc.) can be conjugated with a DTPA dianhydride to obtain not only a desired product but also a by-product of a DTPA bound with two target molecules, the separation process in the above process is complex, and the yield rate is low. So, the prior art does not fulfill users' requests on actual use.

SUMMARY OF THE INVENTION

Therefore, the main purpose of the present invention is to provide a method for manufacturing a DTPA derivative, where the method comprises a simple production procedure with a high yield rate.

To achieve the above purpose, the present invention provides a method for manufacturing a DTPA derivative, which comprises steps of: mixing a DTPA and an ethanol solution to be esterification by a catalyst of sulfuric acid; after being refluxed for 24 hours, removing the solvent and being neutralized with a saturated sodium bicarbonate solution to obtain a penta-ethyl DTPA; mixing the penta-ethyl DTPA, a metal ion and a water as being stirred before adding a strong base solution as being stirred; being bubbled with $H_2S$ to obtain a mixed liquid having a $Cu_2S$ to be filtrated; and being purified with a column to obtain a tetra-ethyl DTPA.

Additionally, the present invention also provides another method for manufacturing a DTPA derivative, which comprises steps of: mixing a diethylenetriamine, a potassium carbonate and an acetonitrile as being stirred under an Ar gas while adding a tert-butyl chloroacetate dissolved in a solution; being deposed under room temperature for chemical reactions for 24 hours before removing the solvent of the solution and filtrating the solution; processing a separation and a purification to obtain a penta-tert-butyl DTPA in a chromatographic column by a mixed solution of an ethyl ether and a hexane; mixing the penta-tert-butyl DTPA, a metal ion and a water as being stirred while adding a strong base of a sodium hydroxide or a potassium hydroxide; being bubbled with $H_2S$ to obtain a mixed solution having $Cu_2S$ to be filtrated with a filter paper; and being purified by a column to obtain a tetra-ethyl DTPA.

In another word, the present invention is a method for manufacturing a DTPA derivative, which comprises steps of at first preparing a penta-alkyl DTPA; and then processing a regioselective hydrolysis over the penta-alkyl DTPA to obtain a tetra-alkyl DTPA while using a metal ion as a catalyst. The alkyl group of the penta-alkyl DTPA and the tetra-alkyl DTPA can be benzyl or $C_nH_{2n+1}$, wherein n is an integer ranging from 1 to 6. In particular, the alkyl group can be chosen from methyl, ethyl, propyl, butyl, pentyl, hexyl, and benzyl. Accordingly, by the above two steps, a monoreactive DTPA derivative is manufactured with simple production procedure and with a yield rate up to at least 51%.

BRIEF DESCRIPTIONS OF THE DRAWINGS

The present invention will be better understood from the following detailed descriptions of the preferred embodiments according to the present invention, taken in conjunction with the accompanying drawings, in which FIG. 1 is a view of the structure of a DTPA (Diethylene Triamine Pentaacetic Acid) according to the present invention;

DESCRIPTION OF THE PREFERRED EMBODIMENTS

The following descriptions of the preferred embodiments are provided to understand the features and the structures of the present invention.

The present invention provides a method for manufacturing a DTPA derivative comprising steps of: mixing a DTPA solution and an ethanol solution in a dehydration apparatus to obtain a mixed solution while processing esterification by adding a catalyst; refluxing the mixed solution for 24 hours to remove the solvent of the mixed solution and neutralizing the mixed solution with a sodium bicarbonate solution to obtain a hazel viscous liquid of a penta-ethyl DTPA; mixing the penta-ethyl DTPA, a metal ion, which can be a cupric chloride, a cupric bromide, a cupric sulfate, a cupric nitrate, a $Pb(NO_3)_2$, a $FeCl_2$, a $CoCl_2$ or a $NiCl_2$, and a water while adding a strong base of a sodium hydroxide or a potassium hydroxide as being stirred for 2 hours to be bubbled with a $H_2S$ to obtain a mixed solution having $Cu_2S$; and filtrating the mixed solution having $Cu_2S$ with a filter paper to be purified by a column to obtain a tetra-ethyl DTPA, whose structure is as follows:

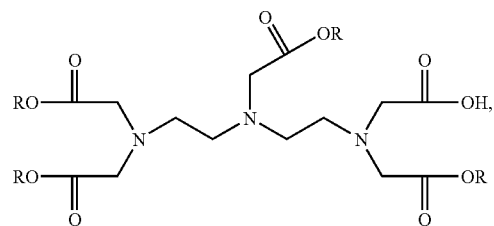

where R=$C_2H_5$—.

In addition, the present invention provides another method for manufacturing a DTPA derivative, comprising steps of:

placing a diethylenetriamine and a potassium carbonate in a flask as being stirred under an Ar gas; being mixed with an acetonitrile before adding a tert-butyl chloroacetate dissolved in an acetonitrile; deposing the flask under room temperature for chemical reactions for 24 hours to remove the solvent of the solution, to filtrate the solution, and to process a separation and a purification to obtain a penta-tert-butyl DTPA in a chromatographic column by a mixed solution of an ethyl ether and a hexane whose mixture rate is 1:10; mixing the penta-ethyl DTPA, a metal ion, which can be a cupric chloride, a cupric bromide, a cupric sulfate, a cupric nitrate, a $Pb(NO_3)_2$, a $FeCl_2$, a $CoCl_2$ or a $NiCl_2$, and a water while adding a strong base of a sodium hydroxide or a potassium hydroxide and being stirred for 2 hours to be bubbled with $H_2S$ to obtain a mixed solution having $Cu_2S$; and being filtrated with a filter paper to be purified by a column to obtain a tetra-tert-butyl DTPA, whose structure is as follows:

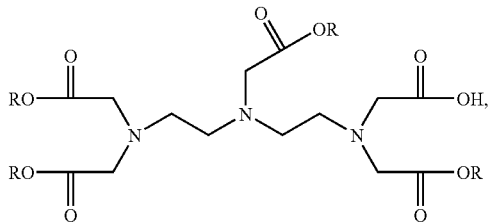

where $R=(CH_3)_3C-$.

The method for manufacturing a DTPA derivative according to the present invention comprises steps of at first preparing a penta-alkyl DTPA and then processing a regioselective hydrolysis to obtain a tetra-alkyl DTPA by using a metal ion as a catalyst. By the above two steps, a monoreactive DTPA derivative can be obtained with a simple production procedure and high yield rate.

For better understanding the present invention, some preferred embodiments are described as follows:

EXAMPLE 1

A Synthesis of a penta-ethyl DTPA

Figure 1:
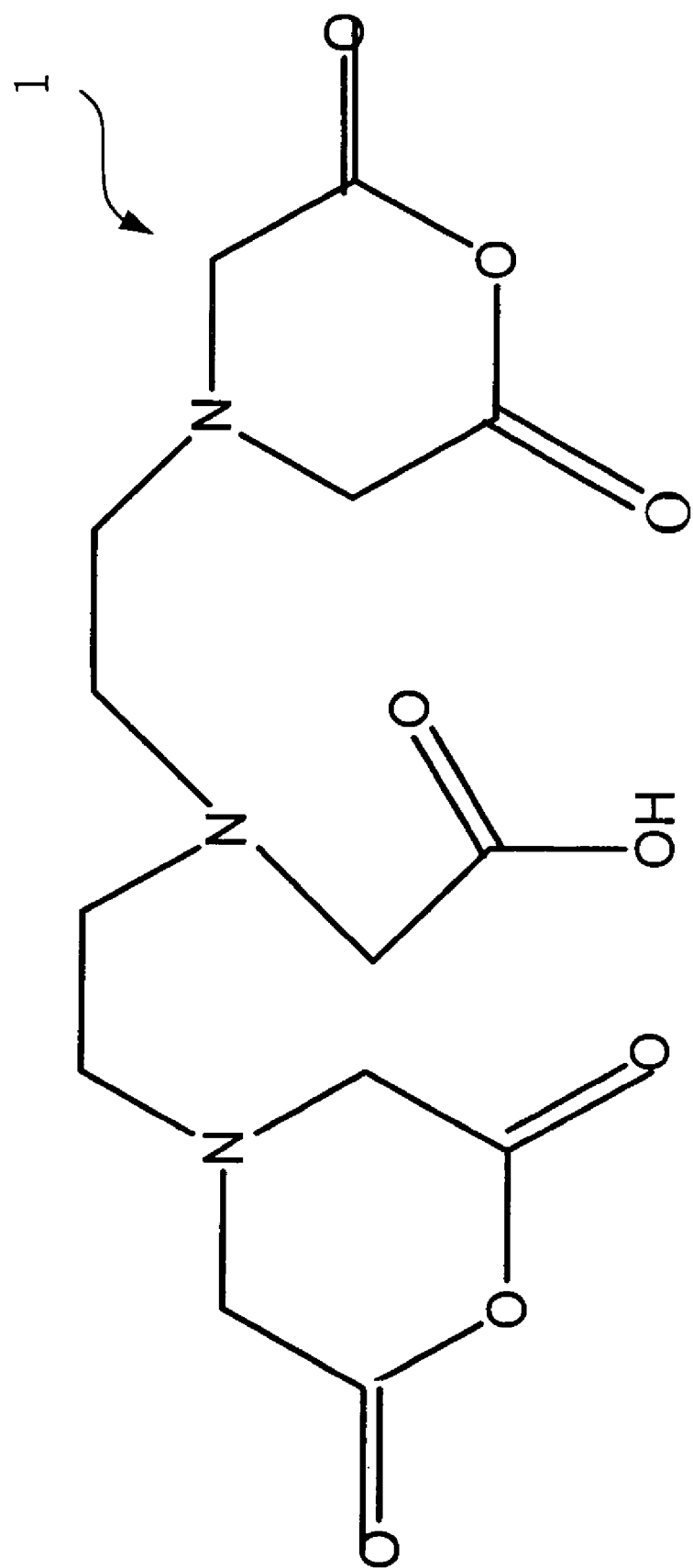
Figure 2:
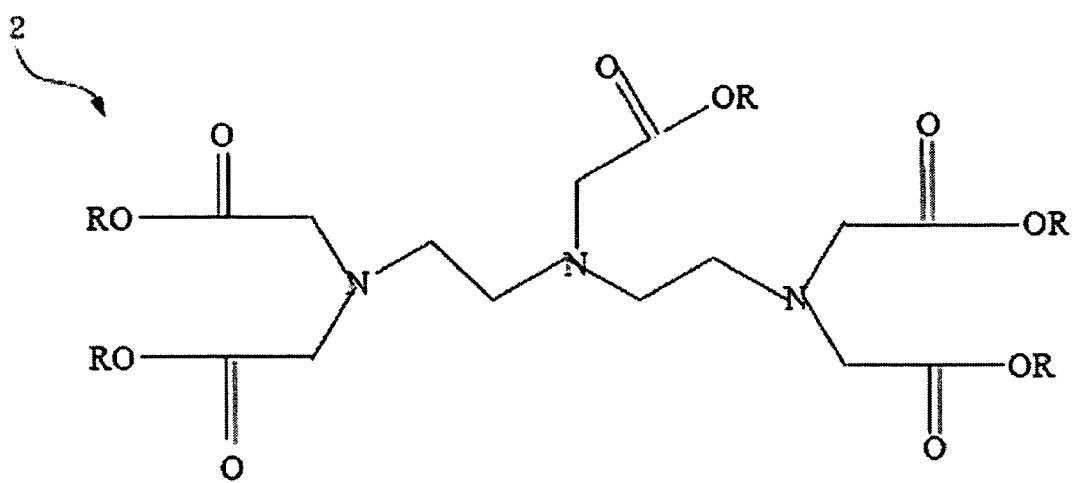
FIG. 2 is a view of the structure of a penta-ethyl DTPA according to the present invention.

Please refer to FIG. 1 and FIG. 2, which are views of the structures of a DTPA and a penta-ethyl DTPA according to the present invention. A 4g(gram) or 0.01 mole of a DTPA 1 is mixed with a 100 ml(milliliter) of ethanol to be catalyzed by dripping a 1.5 ml of sulfuric acid. Because an esterification is reversible reaction while water exists, the solvent is removed by a Dean-Stark apparatus after refluxing for 24 hours. Then, neutralization is processed with a saturate solution of a sodium bicarbonate to obtain a 4.86 g of a hazel viscous liquid of penta-ethyl DTPA 2, whose yield rate is 91%.

$^1$H NMR (Nuclear Magnetic Resonance) ($CDCl_3/\delta$ ppm)
δ 1.16~1.23 (15H 5×—$CH_3$)
δ 2.78~2.84 (8H 2×—N—$CH_2$—$CH_2$—N)
δ 3.43~3.53 (10H 5×—N—$CH_2$—CO)
δ 4.03~4.33 (10H 5×—O—$CH_2$)
$^{13}$C NMR ($CDCl_3/\delta$ ppm)
δ 41.07 δ 128.33
δ 48.85 δ 128.56
δ 50.66 δ 135.57
δ 55.96 δ 169.61
δ 57.08 δ 171.02
δ 66.29

EIMS (electro-ionization mass spectrometer) (m/e %)
($MH^+$)=534
Elemental Analysis (EA) (C, H, N %).
Calculated: C, 54.02%; H, 8.12%; N, 7.87%.
Found: C, 53.74%; H, 8.20%; N, 8.26%.

EXAMPLE 2

A Synthesis of a tetra-ethyl DTPA

Figure 3:
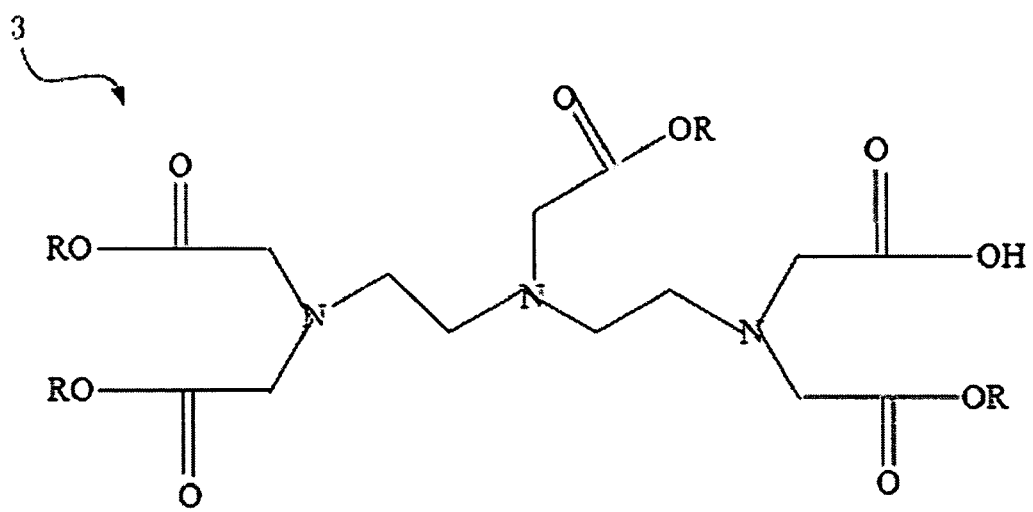
FIG. 3 is a view of the structure of a tetra-ethyl DTPA according to the present invention.

Please refer to FIG. 3, which is a view of the structure of a tetra-ethyl DTPA according to the present invention. The above-mentioned penta-ethyl DTPA 2 (1 g, 1.87 mole) and a $CuCl_2.2H_2O$ (0.318 g, 1.87 millimole) are mixed in 34 ml of water as being stirred for 2 hours while being slowly added with 0.49 ml of sodium hydroxide (0.089 g, 2.244 millimole) solution to obtain a mixed liquid having $Cu_2S$. The mixed liquid is bubbled with $H_2S$ and is filtrated with a filter paper to remove the $Cu_2S$. In the end, through purification by a column, a 0.58 g of viscous tetra-ethyl DTPA 3 is obtained, whose yield rate is 61%. If the cupric chloride is substituted with $NiCl_2$, the yield rate of the tetra-ethyl DTPA 3 can become 56%. If the sodium hydroxide is substituted with a potassium hydroxide, the yield rate of the tetra-ethyl DTPA 3 can become 58%.

$^1$H NMR ($CDCl_3/\delta$ ppm)
δ 1.10~1.16 (m 12H 4×—$CH_3$)
δ 2.75~2.82 (8H 2×—N—$CH_2$—$CH_2$—N)
δ 3.37~3.49 (q 10H 5×—N—$CH_2$—CO)
δ 3.98~4.05 (8H 4×—O—$CH_2$)
δ 10.33 (S 1H —OH)
$^{13}$C NMR ($CDCl_3/\delta$ ppm)
δ 14.10 δ 55.06 δ 170.56
δ 51.03 δ 56.90 δ 170.97
δ 51.45 δ 60.49 δ 173.53
δ 51.94 δ 60.72
δ 53.39 δ 60.83
δ 54.82 δ 170.06
EIMS (m/e %)
($MH^+$)=506
EA (C, H, N %)
Calculated: C, 52.27%; H, 7.78%; N, 8.31%.
Found: C, 51.54%; H, 7.84%; N, 7.92%.

EXAMPLE 3

A Synthesis of a penta-tert-butyl DTPA

Figure 4:
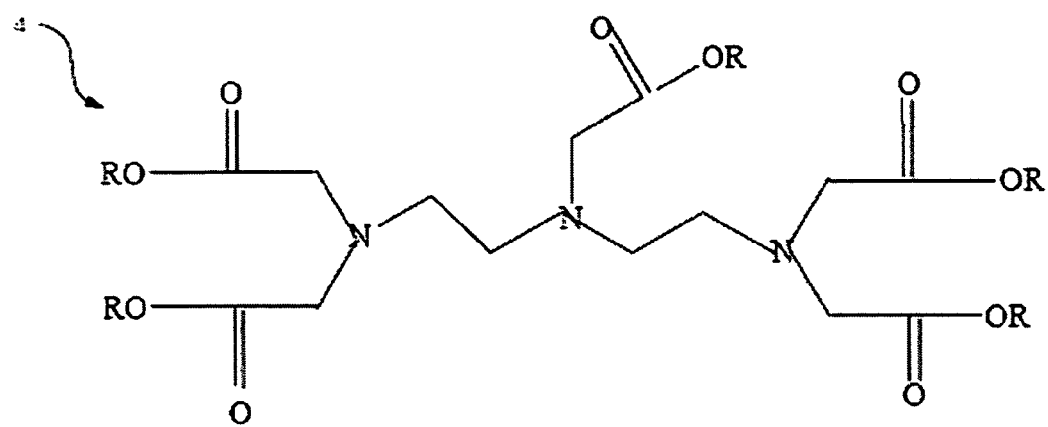
FIG. 4 is a view of the structure of a penta-tert-butyl DTPA according to the present invention.

Please refer to FIG. 4, which is a view of the structure of a penta-tert-butyl DTPA according to the present invention. A diethylenetriamine (2 g, 9.69 millimole), a potassium carbonate (6.7 g) and a 70 ml of acetonitrile are placed in a flask as being stirred. And, a tert-butyl chloroacetate (8.32 ml, 58.16 millimole) dissolved in a 10 ml of acetonitrile is slowly added into the flask to process reactions for 24 hours. Then, the solvent of the solution is removed and the solution is filtrated. The ethyl ether and the hexane are mixed under a mixture rate of 1:10 in a chromatographic column to be separated and purified to obtain a 4.0 g of penta-tert-butyl DTPA 4, whose yield rate is 61%.

$^1$H NMR ($CDCl_3/\delta$ ppm)
δ 1.36 (45H 5×—O—C—$(CH_3)_3$)
δ 2.71 (S 8H 2×—N—$CH_2$—$CH_2$—N)
δ 3.27~3.45 (10H 5×—N—$CH_2$—CO)
$^{13}$C NMR ($CDCl_3/\delta$ ppm)
δ 28.06 δ 55.97 δ 80.72
δ 52.09 δ 76.61 δ 70.55

δ 52.68 δ 77.03
δ 55.67 δ 77.46
EIMS (m/e %)
(MH⁺)=676
EA (C, H, N %)
Calculated: C, 60.60%; H, 9.42%; N, 8.31%.
Found: C, 61.72%; H, 9.51%; N, 8.09%.

EXAMPLE 4

A Synthesis of a tetra-tert-butyl DTPA

Figure 5:
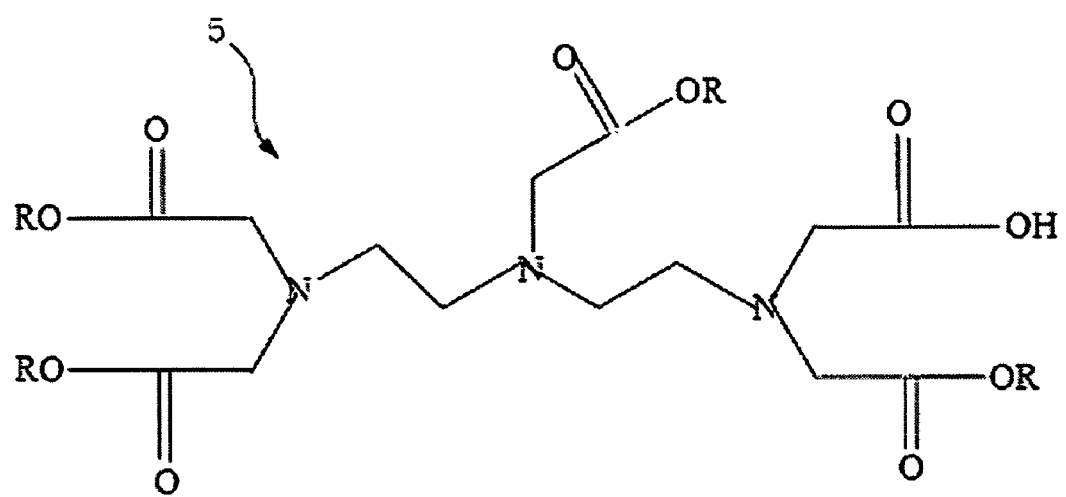
FIG. 5 is a view of the structure of a tetra-tert-butyl DTPA according to the present invention.

Please refer to FIG. 5, which is a view of the structure of a tetra-tert-butyl DTPA according to the present invention. The above-mentioned penta-tert-butyl DTPA 4 and a CuCl₂.2H₂O (0.318 g, 1.87 millimole) are mixed in 34 ml of water as being stirred for 2 hours while slowly adding a 0.49 ml of sodium hydroxide (0.089 g, 2.244 millimole) solution to obtain a mixed liquid. The mixed liquid is bubbled with H₂S and is filtrated with a filter paper to remove the Cu₂S produced while bubbling. In the end, through purification with a column, a tetra-tert-butyl DTPA 5 is obtained, whose yield rate is 51%.

¹H NMR (CDCl₃/δ ppm)
δ 1.24~1.29 (36H 4×—O—C—(CH3)₃)
δ 2.72~2.82 (8H 2×—N—CH₂—CH₂—N)
δ 3.25~3.40 (q 10H 5×—N—CH₂—CO)
δ 9.33 (S 1H —OH)
¹³C NMR (CDCl₃/δ ppm)
δ 27.92 δ 54.48 δ 81.79
δ 50.95 δ 55.64 δ 169.09
δ 51.11 δ 56.42 δ 169.47
δ 51.44 δ 56.78 δ 170.32
δ 51.74 δ 81.08 δ 173.16
EIMS (m/e %)
(MH⁺)=618
EA (C, H, N %)
Calculated: C, 58.33%; H, 9.00%; N, 6.80%.
Found: C, 57.87%; H, 9.12%; N, 6.62%.

To sum up, a method for manufacturing a DTPA derivative according to the present invention uses a strategy of "a regioselective hydrolysis by adding a strong base solution with a metal ion as a catalyst" to simplify production procedure while having a high yield rate.

The preferred embodiments herein disclosed are not intended to unnecessarily limit the scope of the invention. Therefore, simple modifications or variations belonging to the equivalent of the scope of the claims and the instructions disclosed herein for a patent are all within the scope of the present invention.

What is claimed is:

1. A method for manufacturing a tetra-alkyl DTPA (Diethylene Triamine Pentaacetic Acid), comprising:
   (a) mixing a solution of DTPA and an alcohol in the presence of a catalyst in a dehydration apparatus;
   (b) refluxing said solution for 24 hours and neutralizing said solution with a sodium bicarbonate solution to obtain a penta-alkyl DTPA;
   (c) mixing said penta-alkyl DTPA, metal ion, and water and stirring for 2 hours while adding a strong base to obtain a solution comprising Cu₂S and bubbling said solution comprising Cu₂S with H₂S, wherein said metal ion is selected from the group consisting of cupric chloride, cupric bromide, cupric sulfate and cupric nitrate; and
   (d) filtering said solution having Cu₂S with filter paper, and obtaining a tetra-alkyl DTPA by column chromatography.

2. The method for manufacturing a tetra-alkyl DTPA according to claim 1, wherein said alcohol is ethanol.

3. The method for manufacturing a tetra-alkyl DTPA according to claim 1, wherein said catalyst is sulfuric acid.

4. The method for manufacturing a tetra-alkyl DTPA according to claim 1, wherein said penta-alkyl DTPA is a hazel viscous liquid.

5. The method for manufacturing a tetra-alkyl DTPA according to claim 1, wherein said strong base is selected from the group consisting of sodium hydroxide and potassium hydroxide.

6. The method for manufacturing a tetra-alkyl DTPA according to claim 1, wherein the structure of said tetra-alkyl DTPA is:

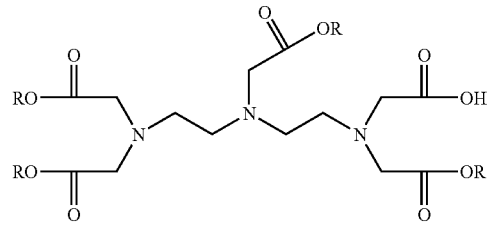

and wherein said R is benzyl or —$C_nH_{2n+1}$, wherein n is an integer ranging from 1 to 6.

7. The method for manufacturing a tetra-alkyl DTPA according to claim 6, wherein said R is —$C_2H_5$.

8. A method for manufacturing a tetra-alkyl DTPA (Diethylene Triamine Pentaacetic Acid), comprising:
   (a) mixing a solution of diethylenetriamine, potassium carbonate, and acetonitrile with stirring and under Ar gas in a flask, while adding a reagent capable of forming a penta-alkyl DTPA with said solution;
   (b) reacting the contents of said flask for 24 hours at room temperature, then removing the solvent from said flask and filtering the remaining contents of said flask, then using a mixture of ethyl ether and hexane in column chromatography to obtain a penta-alkyl DTPA from said filtered remaining contents of said flask;
   (c) mixing said penta-alkyl DTPA, metal ion, and water and stirring for 2 hours while adding a strong base to obtain a solution comprising Cu₂S and bubbling said solution comprising Cu₂S with H₂S, wherein said metal ion is selected from the group consisting of cupric chloride, cupric bromide, cupric sulfate and cupric nitrate; and
   (d) filtering said solution having Cu₂S with filter paper, and obtaining a tetra-alkyl DTPA by column chromatography.

9. The method for manufacturing a tetra-alkyl DTPA according to claim 8, wherein said mixture of ethyl ether and hexane is 1:10.

10. The method for manufacturing a tetra-alkyl DTPA according to claim 8, wherein said strong base is selected from the group consisting of sodium hydroxide and potassium hydroxide.

11. The method for manufacturing a tetra-alkyl DTPA according to claim 8, wherein the structure of said tetra-alkyl DTPA is:

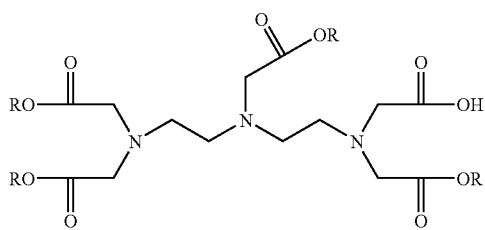
and wherein said R is benzyl or —$C_nH_{2n+1}$, wherein n is an integer ranging from 1 to 6.
12. The method for manufacturing a tetra-alkyl DTPA according to claim 11, wherein said R is $(CH_3)_3C-$.
13. The method for manufacturing a tetra-alkyl DTPA according to claim 8, wherein said reagent is tert-butyl chloroacetate dissolved in acetonitrile.
* * * * *